United States Patent
Martin

(10) Patent No.: US 10,545,234 B2
(45) Date of Patent: Jan. 28, 2020

(54) METHOD AND SYSTEM FOR DETECTING AIRCRAFT INDUCED WAKE TURBULENCE

(71) Applicant: Windbidco Pty Ltd, Ferny Creek (AU)

(72) Inventor: Andrew Louis Martin, Ferny Creek (AU)

(73) Assignee: Windbidco Pty Ltd, Ferny Creek (AU)

( * ) Notice: Subject to any disclaimer, the term of this patent is extended or adjusted under 35 U.S.C. 154(b) by 399 days.

(21) Appl. No.: 15/306,926

(22) PCT Filed: Apr. 21, 2015

(86) PCT No.: PCT/AU2015/000238
§ 371 (c)(1),
(2) Date: Oct. 26, 2016

(87) PCT Pub. No.: WO2015/164905
PCT Pub. Date: Nov. 5, 2015

(65) Prior Publication Data
US 2017/0045615 A1 Feb. 16, 2017

(30) Foreign Application Priority Data
Apr. 28, 2014 (AU) .............................. 2014901525

(51) Int. Cl.
*G01S 15/88* (2006.01)
*G01N 29/02* (2006.01)
(Continued)

(52) U.S. Cl.
CPC .............. *G01S 15/885* (2013.01); *B64F 1/36* (2013.01); *G01N 29/02* (2013.01); *G01W 1/00* (2013.01);
(Continued)

(58) Field of Classification Search
CPC .... G01S 15/885; G01S 15/003; G01S 15/104; G01N 29/02; G01N 2291/044;
(Continued)

(56) References Cited

U.S. PATENT DOCUMENTS 5,519,618 A * 5/1996 Kastner ................... G01S 13/91
701/120
7,284,421 B2 10/2007 Martin
(Continued)

OTHER PUBLICATIONS

The Examination Report dated Jan. 4, 2018, in EP15786557.7.
The International Search Report and Written Opinion dated May 27, 2015, in PCT/AU2015/000238, filed Apr. 21, 2015.
Frech, Michael "Estimating the turbulent energy dissipation rate in an airport environment," Boundary-Layer Meteorol, Feb. 20, 2007, pp. 385-393, vol. 123.

*Primary Examiner* — Daniel S Larkin
*Assistant Examiner* — Anthony W Megna Fuentes
(74) *Attorney, Agent, or Firm* — Hovey Williams LLP

(57) ABSTRACT

A method is disclosed for detecting atmospheric turbulence including aircraft induced wake turbulence and/or wind shear within an aperture associated with an aircraft approach or departure corridor around an airport. The method comprises transmitting into the aperture acoustic signals having a waveform suitable for pulse compression and receiving backscattered acoustic echoes of the acoustic signals from the atmospheric turbulence and/or wind shear. The method further includes processing the acoustic echoes in a matched filter receiver to provide a measure of the atmospheric turbulence and discriminating the aircraft induced demise time, being a time taken for the aircraft induced wake turbulence and/or wind shear to fall below a set threshold at least in the aperture. A system for detecting atmospheric turbulence including aircraft induced wake turbulence and/or wind shear associated with an aircraft approach or departure corridor around an airport is also disclosed.

20 Claims, 15 Drawing Sheets

(51) Int. Cl.
*B64F 1/36* (2017.01)
*G01W 1/00* (2006.01)
*G08G 5/00* (2006.01)
*G01S 15/10* (2006.01)
*G01S 15/00* (2006.01)

(52) U.S. Cl.
CPC ............... *G01N 2291/0215* (2013.01); *G01N 2291/044* (2013.01); *G01W 2001/003* (2013.01)

(58) Field of Classification Search
CPC .... G01N 2291/0215; B64F 1/36; G01W 1/00; G01W 2001/003; G08G 5/0091
See application file for complete search history.

(56) References Cited

U.S. PATENT DOCUMENTS

| | | | |
|---|---|---|---|
| 7,703,319 B2 | 4/2010 | Martin | |
| 2002/0042673 A1* | 4/2002 | Ooga | G01S 7/04 |
| | | | 701/120 |
| 2009/0107232 A1* | 4/2009 | Martin | G01S 15/003 |
| | | | 73/170.13 |
| 2010/0046325 A1* | 2/2010 | Martin | G01S 15/104 |
| | | | 367/87 |

\* cited by examiner

METHOD AND SYSTEM FOR DETECTING AIRCRAFT INDUCED WAKE TURBULENCE

RELATED APPLICATIONS

This is a national stage application under 35 U.S.C. § 371 of International Patent Application No. PCT/AU2015/000238, filed Apr. 21, 2015, which claims the benefit of Australian Patent Application No. 2014901525, filed Apr. 28, 2014, both of which are incorporated by reference herein in their entireties.

TECHNICAL FIELD

The present invention relates to the field of SODAR systems for use in atmospheric sounding and in particular relates to a method and system for detecting aircraft induced wake turbulence and/or wind shear within an aperture associated with an aircraft approach or departure corridor around an airport. The method and system may detect aircraft induced wake turbulence and/or wind shear in real time and may measure a time to demise of the turbulence.

BACKGROUND TO THE INVENTION

A need to detect aircraft induced wake vortices and associated turbulence is well established and is set out in a program in Europe named SESAR, http://www.sesarju.eu/, and in a similar program in North America called NextGen, http://www.faa.gov/nextgen/. These two programs are summarised in the ICAO ASBU document, http://www.icao.int/sustainability/Pages/ASBU-Framework.aspx. In order to meet the objectives of these programs there is a need for a technology and systems that can detect the position and strength of aircraft induced wake turbulence in real time and in all weather conditions. In particular there is a need for a system that can detect wake turbulence in the approach or departure corridors of an airport, being critical regions wherein a following aircraft encountering wake turbulence from a leading aircraft can suffer an upset which can have severe consequences.

The wake from an aircraft arises because of displacement of air required to generate lift. This wake can evolve into several forms, all of which are potentially hazardous for following aircraft. The wake can roll up into a vortex which may last from 20 seconds to several minutes depending on atmospheric conditions. The vortices can have a variety of states which may include core vortices with core diameters of around 1 m that rotate at between 80 and 200 m/s and which may be wrapped into large core vortices with a diameter up to 30 m that rotate at between 5 and 20 m/s. The vortices always have strong air turbulence or wind shear associated with them which can disrupt the flight of an aircraft encountering it. Sometimes the aircraft induced wake may evolve directly into turbulence without going through a vortex stage. Thus any process to measure safety of an approach corridor should be capable of detecting all aircraft induced wakes. Since turbulence is always associated with an aircraft wake then a reliable arrangement is to directly detect wake turbulence. However, detecting aircraft induced wake vortices alone may not be sufficient to ensure that an approach corridor is safe for a following aircraft from turbulence induced or generated by a leading aircraft.

Various approaches to detecting aircraft induced wake vortices have used RADAR, LIDAR and SODAR wherein the aim is to detect position of wake vortices so that they can be tracked. There have also been several attempts to measure strength of aircraft induced wake vortices, some have been successful and some not so successful. A summary of these efforts is given in:
http://ntl.bts.gov/lib/33000/33700/33701/WakeNet3_Europe_March2010_Sensor_Volpe.pdf.

The above efforts have not yielded a system that can reliably detect all types of aircraft induced wake turbulence in real time and in all weather conditions as is required for an operational system to deliver the benefits outlined in the SESAR, NextGen or the ICAO ASBU programs.

A known aircraft vortex system outlined in U.S. Pat. No. 3,671,927 uses refraction of sound waves for detecting wake vortices but can detect only a few of the vortices present. This occurs because the technique can only detect one of the pair of aircraft induced vortices that have a rotational velocity greater than about 80 m/s (http://ntl.bts.gov/lib/46000/46000/46025/Burnham_CharacteristicsWake_VortexTracking.pdf) and consequently cannot also detect slower vortices or turbulence associated with an aircraft wake which is also present. Thus the system in U.S. Pat. No. 3,671,927 may not provide a reliable indication of aircraft induced wake vortices and/or turbulence.

A known acoustic wind sensor also outlined in U.S. Pat. No. 3,671,927 has limitations in that it can only detect vortices that are in the beam of a single transmitter by using a scanning receiver beam and there is thus a much lower probability of detection than is required for an operational system. A similar system is outlined in "Doppler Acoustic Vortex Sensing System by R. P. McConville" in: http://www.dtic.mil/dtic/tr/fulltext/u2/a062026.pdf, wherein both pulsed and CW acoustic systems for detecting aircraft wake vortices are described. In particular FIG. 3-34 shows Backscatter Pulsed, Forward scatter Pulsed and Forward Scatter CW systems. A pictorial diagram of a Forward Scatter CW system is given in FIG. 4-1. A CW system inherently has no range information, however range can be obtained by sweeping transmitter and/or receiver beams.

Previous attempts to detect wake vortices using a chirp based SODAR outlined in Applicant's U.S. Pat. No. 7,284,421 entitled Detection of wake vortices and the like, and U.S. Pat. No. 7,703,319 entitled Characterisation of Aircraft Wake Vortices, consisted of refraction of an acoustic signal having a pulse compression waveform (chirp) by the core of the vortex. This system gave accurate measurements of vortex height providing that the vortex core rotated at a velocity of greater than 80 m/s, but could not reliably detect vortices that rotated at less than 80 m/s or turbulence associated with an aircraft wake because the backscattered signal-to-noise ratio was too low to be detectable and because no reliable information on strength or decay time of all aircraft induced wake turbulence could be obtained. Poor detection of all aircraft related turbulence in the flight path was due to a single transmitter antenna only partially illuminating the area above the antenna with sufficient transmitted signal to obtain the necessary signal-to-noise ratio and coverage width of the flight path to provide a useful "synthetic aperture". Thus U.S. Pat. No. 7,284,421 fails to detect all aircraft generated wake vortices and turbulence in a "synthetic aperture" that is necessary to determine whether the flight path is safe for a following aircraft.

Chirp based SODAR disclosed in Applicant's U.S. Pat. No. 6,755,080 entitled Acoustic Sounding, U.S. Pat. No. 7,317,659 entitled Measurement of the Air Characteristics of the Lower Atmosphere and U.S. Pat. No. 7,178,408 entitled SODAR Sounding of the Lower Atmosphere, has 45 dB more gain than a conventional short pulse SODAR and 25 dB more gain than chirp SODAR systems disclosed in other prior art. The latter systems use each amplitude measurement independently at an update rate of the chirp SODAR to provide a wake turbulence measurement. The latter systems improve on the prior art by using a chirp signal format with relatively high chirp rates (eg. at least 1000 Hz/second), by using IIR window linear phase filters in a matched filter receiver, and by using an improved antenna design. Chirp acoustic signals belong to a class of waveforms known to be suitable for use in a pulse compression or matched filter receiver. A good introduction to pulse compression waveforms and matched filters is given in "Introduction to Radar Systems, Third Edition, by Merrill I. Skolnik, McGraw Hill, 2001, ISBN 0-07-118189-X.

An improved antenna design includes double side walls with internal acoustic absorbers for maximum isolation as well as offset feed antennas with relatively low side lobes. The antenna design also includes a relatively high efficiency compression driver enabling sound levels up to 135 dBa to be transmitted. This may enable the chirp SODAR to measure substantially all types of atmospheric turbulence in real time without averaging, a capability that was not previously available to any SODAR, LIDAR or RADAR system. Measurement of turbulence may be achieved when acoustic energy is backscattered from small scale temperature discontinuities and/or fluctuations in the atmosphere.

Safe aircraft apertures for arrival and departure have been previously discussed in: http://www.transportresearch.info/Upload/Documents/201208/20120807_184001_3122_ATC_Wake%20D2_12.pdf.

The aperture disclosed in the latter reference is in the context of showing how modelled wake vortices may be depicted in terms of the aircraft corridor, although no suggestion is given to applying the concept to real time measurement of wake turbulence or the method to implement such real time measurement system. For example, U.S. Pat. No. 7,284,421 discloses a "synthetic aperture" but does not disclose how to build a system with a non-synthesised aperture.

Many attempts have been made over the past 30 years to produce a predictive system based on wake vortex behaviour modelling for estimating aircraft wake vortex position and demise times. However, some sections of the aviation community have questioned the viability of predictive/inferential information in place of real-time measurements of the vortices. Thus as far as applicant is aware, there is no known acoustic pulse compression system that indicates how to measure aircraft wake turbulence in an aperture in real time for the purpose of obtaining safe aircraft spacing within an approach or departure corridor.

The term turbulence as used herein denotes small-scale, irregular air motions characterised by winds that vary in speed and/or direction. Turbulence is significant because it mixes and churns the atmosphere and causes water vapour, smoke, and other substances, as well as energy, to become distributed both vertically and horizontally.

The term aperture as used herein denotes a slice or cross-section along an approach or departure corridor near an airport. The aperture contains a region within which an aircraft generates or induces turbulence and through which a following aircraft passes after a leading aircraft induces wake turbulence. The term aperture may also denote the whole of an area within which wake turbulence induced by an aircraft may travel between different aircraft corridors including approach and departure corridors.

The table below shows that chirp based SODAR is a technology that can meet the requirements of an aircraft wake turbulence measurement system. LIDAR or RADAR solutions cannot achieve anywhere near the level of performance set out in the table because of resolution and update rate limitations. The update rate in the table is important because sufficient time resolution is required to ensure that turbulence in an aperture is clear so that aircraft spacing can be optimised.

| Aperture Aircraft Wake Turbulence Measurement Requirements Table | | | | | | |
|---|---|---|---|---|---|---|
| | Update rate | Resolution | Averaging | Min Range | Max Range | Coverage Width |
| Requirements | <5 Sec | 5 m | No Averaging | 10 m | 150 m | 150 m |
| Short Pulse SODAR | 20 sec | 10 m | Averages to get data | 40 m | 50 m | 150 m With array |
| Chirp SODAR | <5 sec | 2 m | No Averaging used | 10 m | 250 m | 150 m with array |

Most work to date has concentrated on measuring aircraft wake vortex trajectories and then trying to develop models of this behaviour. This has not been successful because many parameters required to describe wake vortex behaviour are highly variable and difficult or impossible to obtain in practice.

The wake vortex problem is complex precisely because a large number of parameters are involved. Setting aside various operational scenarios, the problem involves parameters introduced by vortex-generating aircraft, by vortex-encountering aircraft, and by the intervening atmosphere. The vortex is initially characterized by parameters of the vortex-generating aircraft including weight, wingspan, speed, flap and spoiler settings, proximity to the ground, engine thrust, lift distribution, etc. The encounter (safe or hazardous) is characterized by parameters of the following aircraft including speed, wingspan, roll control authority, phase of flight, etc. Meteorology variables including wind, crosswind, atmospheric stability, background atmospheric turbulence, etc. also plays a critical role in determining how long a vortex may remain hazardous.

Current separation times between aircraft arriving and departing airports have been set conservatively to minimize turbulence encounter. The settings are generally conservative and rely on estimated demise or transit of turbulence out of departure or arrival corridors within a separation time, without any actual measurement of position or strength of wake turbulence being made within the corridors.

The present applicant recognizes that there is considerable potential to reduce aircraft separation times on arrival and departure if it was possible to determine in real time how long it takes for the wake turbulence from a leading aircraft to reduce to a safe threshold within the approach or departure corridor. Determination of a safe threshold for aircraft wake turbulence is relatively complex as different aircraft can tolerate different levels of turbulence. The determination may be further complicated by presence of normal or background atmospheric turbulence which itself is highly variable. Thus to correctly measure an actual safe turbulence threshold requires a prior knowledge of the state of the atmospheric background turbulence as well. Determination of a safe threshold for aircraft wake turbulence in real time may lead not only to better capacity and utilization of airport infrastructure but also to improved safety.

The method and system of the present invention may measure atmospheric turbulence in an aperture including turbulence generated or induced by an aircraft in the aperture, a means of determining different types of turbulence in the aperture and a demise time, being a time taken for the aircraft generated or induced turbulence to fall to or below a set or safe level or threshold within the aperture. If the demise time is measured in real time, then a reasonable safety or time buffer or margin may be applied to determine a safe or optimum spacing time for a following aircraft to pass through the aperture.

A reference herein to a patent document or other matter which is given as prior art is not to be taken as an admission or a suggestion that that document or matter was known or that the information it contains was part of the common general knowledge as at the priority date of any of the claims.

Where the terms "comprise", "comprises", "comprised" or "comprising" are used in this specification (including the claims) they are to be interpreted as specifying the presence of the stated features, integers, steps or components, but not precluding the presence of one or more other feature, integer, step, component or group thereof.

SUMMARY OF THE INVENTION

According to one aspect of the present invention there is provided a method for detecting atmospheric turbulence including aircraft induced wake turbulence and/or wind shear within an aperture associated with an aircraft approach or departure corridor around an airport, said method comprising: transmitting into said aperture acoustic signals having a waveform suitable for pulse compression; receiving backscattered acoustic echoes of the acoustic signals from said atmospheric turbulence and/or wind shear; processing the acoustic echoes in a matched filter receiver to provide a measure of said atmospheric turbulence; and discriminating said aircraft induced wake turbulence to determine a demise time, being a time taken for said aircraft induced wake turbulence and/or wind shear to fall below a set threshold at least in said aperture.

Preferably the acoustic signals comprise chirps with a frequency variation rate that is at least 1 kHz per second to reduce range error and/or optimize resolution. In one preferred embodiment plural said acoustic signals may be transmitted via plural transmitter antennas. The plural transmitter antennas may be placed substantially across the aircraft approach or departure corridor to obtain acceptable coverage of an aperture. The plural acoustic signals may be transmitted substantially on the same frequency and may include positive and negative chirps. In another preferred embodiment the plural acoustic signals may be transmitted on different frequencies and may include positive and negative chirps.

The backscattered acoustic echoes may be received via plural receiver antennas. The plural receiver antennas may be placed substantially across the aircraft approach or departure corridor to obtain acceptable coverage of an aperture.

The processing may include emulating the matched filter receiver to determine a magnitude of the backscattered acoustic echoes received via the plural receiver antennas, the magnitude being indicative of a level of the turbulence and/or wind-shear within the aperture. The method may include discriminating or differentiating between aircraft induced wake turbulence and background atmospheric turbulence being other than aircraft induced wake turbulence. The method may further include comparing amplitude from each receiver antenna to establish a horizontal location of the turbulence and/or wind shear.

A demise time may be calculated substantially along an entire aircraft approach or departure corridor. The method may include deriving an estimated turbulence demise time from a wind profile and correcting the estimated demise time profile with an actual turbulence demise time obtained at one or more apertures.

Correcting may be performed by applying interpolation along the aircraft approach or departure corridor using actual demise time obtained from one or apertures together with measured wind profiles to obtain actual aircraft wake turbulence demise times along the aircraft approach or departure corridor. A safety margin may be added to the demise times to obtain an aircraft spacing time. Preferably the threshold is set such that it is relatively safe for a following aircraft to pass through the aperture.

According to a further aspect of the present invention there is provided a system for detecting atmospheric turbulence including aircraft induced wake turbulence and/or wind shear within an aperture associated with an aircraft approach or departure corridor around an airport, said system comprising: at least one transmitter antenna for transmitting into said aperture acoustic signals having a waveform suitable for pulse compression; at least one receiver antenna for receiving backscattered acoustic echoes of the acoustic signals from said atmospheric turbulence and/or wind shear; a matched filter receiver for processing the acoustic echoes to provide a measure of said atmospheric turbulence and means for discriminating said aircraft induced wake turbulence to determine a demise time, being the time taken for said aircraft wake turbulence and/or wind shear to fall below a set threshold at least in said aperture.

DESCRIPTION OF DRAWINGS

Preferred embodiments of the present invention will now be described with reference to the accompanying drawings wherein.

DESCRIPTION OF PREFERRED EMBODIMENTS OF THE INVENTION

Figure 1:
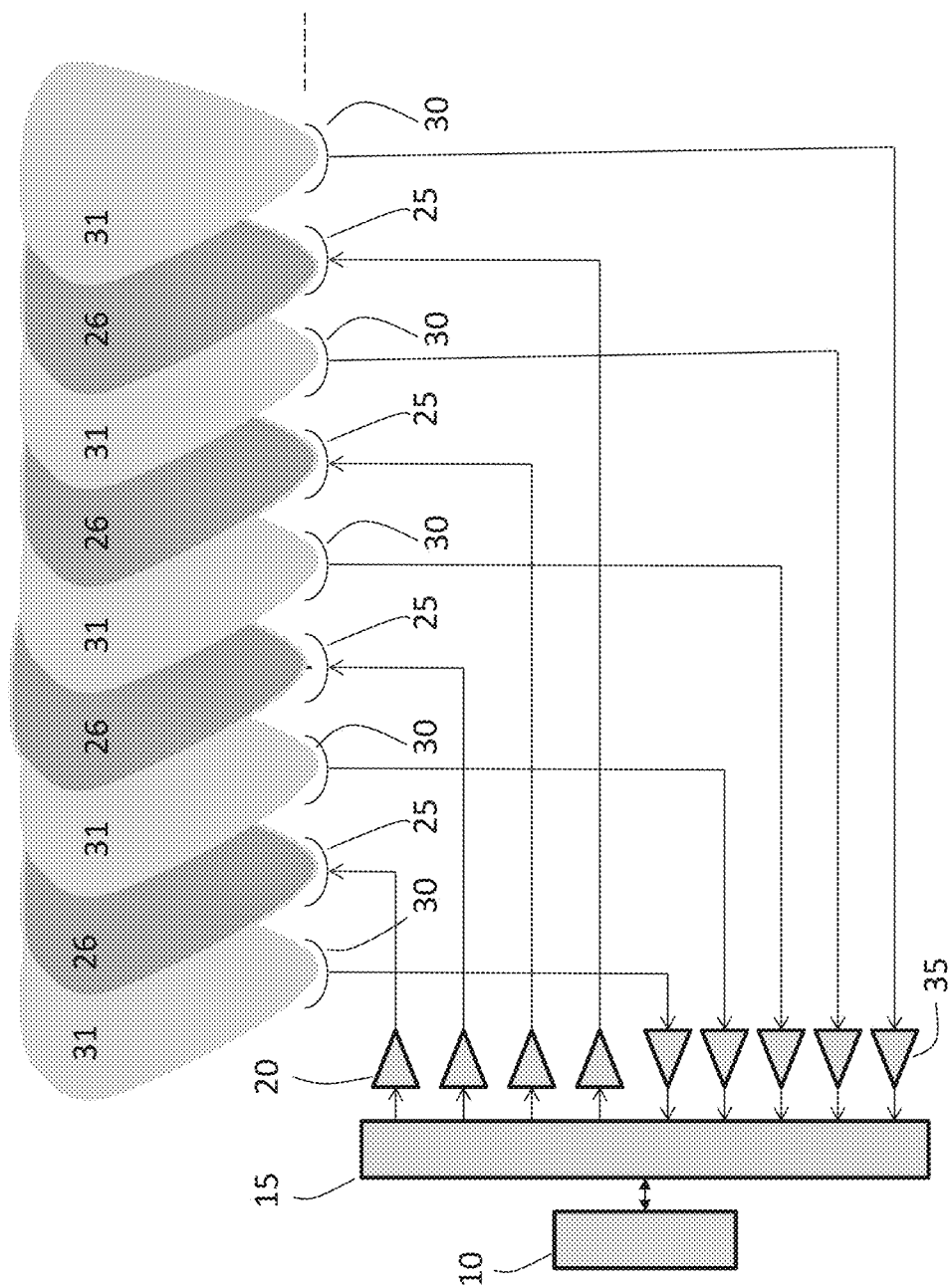
FIG. 1 shows a generic acoustic chirp system for determining presence of aircraft wake turbulence in an aperture along an approach or departure corridor around an airport.

The present invention may provide an improved method and system for detecting aircraft induced wake turbulence and/or wind shear in an aperture or section of an aircraft arrival or departure corridor around an airport. The present invention may reliably detect presence of various types of background atmospheric and aircraft induced wake turbulence in the aperture. This may be done by repeatedly transmitting a beam of acoustic chirp signals and repeatedly measuring amplitude of received or backscattered acoustic echo signals to establish that wake turbulence is present in the aperture. The backscattered acoustic echo technique may detect various types of aircraft wake turbulence in all weather conditions.

To obtain sufficient coverage of an aperture for location of turbulence in real time, several transmitters and receivers may be used to cover the aperture. By using several chirp signal transmitters and receivers with substantially vertical directed beams, an aperture orthogonal to a flight path corridor may be covered avoiding a need to scan a single beam or need to construct a synthetic aperture. Such an arrangement may significantly improve probability of detecting wake turbulence in an aperture of a flight path corridor by minimising time taken to obtain a reading across an entire aperture.

An advantage of this approach is that a measure of distance of the turbulence from the transmitter may be available which may enable the turbulence to be located within the aperture. Once the turbulence is located and its level is determined, the time, after an aircraft has passed through the aperture for the turbulence to fall below a safe or set threshold may be measured using repeated measurements of turbulence. Because the system is adapted to measure turbulence, a lack of turbulence may suggest that the aperture is safe for a following aircraft.

The amplitude of signals received over a range of receivers may be used to determine a likely horizontal position of the most severe turbulence. The acoustic chirp signal used for each transmitter may include a single frequency band. Alternatively different frequency bands may be used for each transmitter to provide additional horizontal discrimination of location of the turbulence. The number of available frequency bands may be doubled if chirps with increasing frequencies and chirps with decreasing frequencies are used. If a horizontal location is known, the turbulence may be tracked horizontally to provide additional information about when the turbulence has fallen below a safe or set threshold.

The strength of the turbulence is directly related to amplitude of the return signal. This means that measuring the time it takes for the turbulence to fall to a safe or set level or threshold after an aircraft has passed may provide a relatively straight forward metric of demise time. The threshold level may need to be adjusted depending on the level of atmospheric turbulence. The demise time or time taken for the turbulence to fall to the set threshold may be highly variable and may depend, among other things, on aircraft type, flap settings, weight, cross wind and atmospheric turbulence. Such variability means that real time measurements are required to obtain a reliable value for the turbulence demise time.

The turbulence demise time in an aperture of a flight corridor, may be combined via interpolation with wind profile information along the approach or departure corridor in order to estimate the time that it will take for the turbulence to exit the entire corridor. Cross wind may determine the time it takes wake turbulence to exit the approach or departure corridor. Since the wind varies with height, turbulence demise time will also vary along the approach or departure corridors. Additional apertures may be added along the approach or departure corridor in order to improve estimates of turbulence exit time from the corridor.

FIG. 1 shows a generic acoustic chirp system for determining presence of aircraft wake turbulence in an approach or departure corridor around an airport. The system includes a computer 10, a sound card 15 attached to the computer 10, power amplifiers 20, plural transmitter antennas 25, plural receiver antennas 30 and associated receiver preamplifiers 35. Computer 10 generates chirp signals having a pulse compression waveform which are sent to sound card 15 and then to audio power amplifiers 20 and transmitter antennas 25.

Each transmitter antenna 25 produces an acoustic transmitter beam 26 and each receiver antenna 30 has a receiver lobe pattern 31. Each transmitter antenna 25 has a receiver antenna 30 on each side to provide coverage of a section of aperture 60 as shown in FIG. 2, so that an entire corridor may be covered using several transmitter and receiver antennas.

Each transmitter antenna 25 emits an acoustic chirp signal which may be of the same or different frequencies. The beam 26 of each transmitter antenna 25 and the lobe pattern 31 of each receiver antenna 30 may overlap as shown in FIG. 1 to provide a coverage area that is equal to the transmitter beam 26 for that transmitter receiver pair. Chirp signals backscattered from aircraft induced wake turbulence are captured by the receiver lobe pattern 31 of receiver antenna 30, passed to receiver preamplifier 35, sound card 15 and to computer 10 where a matched filter receiver is implemented (refer FIG. 15) to obtain a measure of wake turbulence.

Wake turbulence is created by wings of an aircraft passing through aperture 60 and will appear in different receiver beams 31 allowing an approximate horizontal location of relatively high turbulence (e.g. 205 in FIG. 9) to be determined. Once high turbulence dissipates or leaves aperture 60 due to wind blowing it away, relatively low turbulence (e.g. 185 in FIG. 8) may no longer be a hazard to a following aircraft. The dimensions of aperture 60 will depend on its location with respect to an airport runway.

Figure 2:
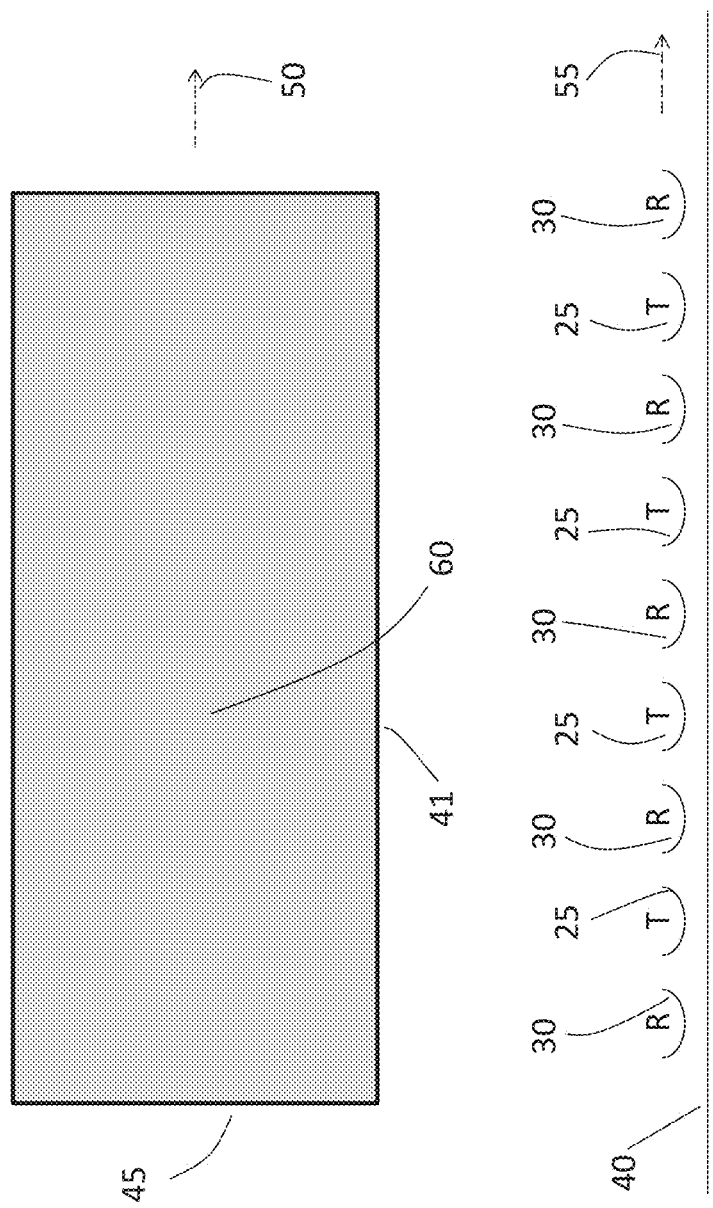
FIG. 2 shows an array of separate transmitter and receiver antennas relative to an aperture within which turbulence is to be measured.

FIG. 2 shows a general relationship between transmitter antennas 25, receiver antennas 30 and aperture 60. Aperture 60 has a height 45 and a width 41 and will normally be above ground 40. Transmitter antennas 25 and receiver antennas 30 are arranged underneath aperture 60 so as to provide adequate coverage of aperture 60. A larger aperture 60 may be covered by adding more transmitter and receiver antennas 55 in the direction of arrow 50.

Figure 3:
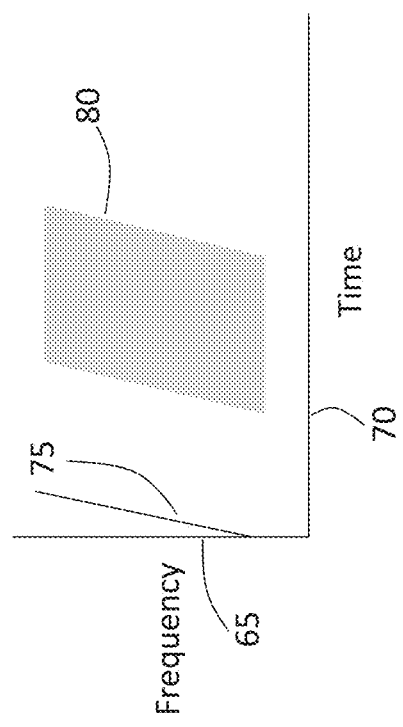
FIG. 3 shows a forward transmitted chirp signal and received echo signals.

FIG. 3 shows a forward transmitted chirp signal 75 and echo signals 80 of the chirp signal received from aperture 60. The forward chirp signal 75 has a frequency range 65 of say 1000 Hz and increases over a time segment 70 of say one second, to produce a chirp rate of 1000 Hz/second. Different chirp parameters may be used but the chirp rate should be sufficiently high to avoid range error and/or optimize resolution. Echo signals 80 will be received from aperture 60 after chirp 75 is transmitted.

Figure 4:
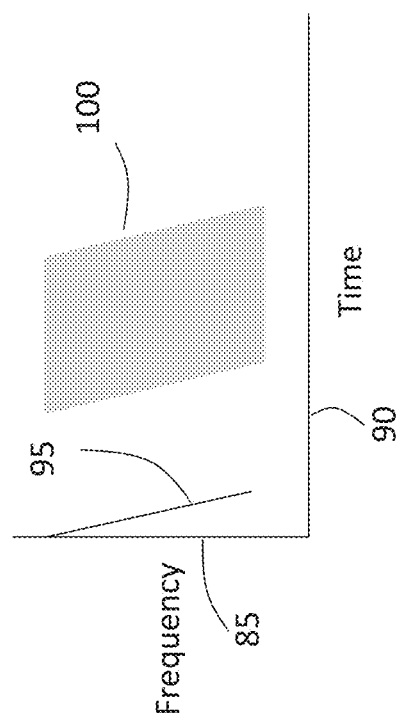
FIG. 4 shows a reverse transmitted chirp signal and received echo signals.

FIG. 4 shows a reverse transmitted chirp signal 95 and echo signals 100 received from aperture 60. The reverse chirp signal 95 has a frequency range 85 of say 1000 Hz and decreases over a time segment 90 of say one second. Echo signals 100 will be received from aperture 60 after chirp 95 is transmitted.

Figure 5:
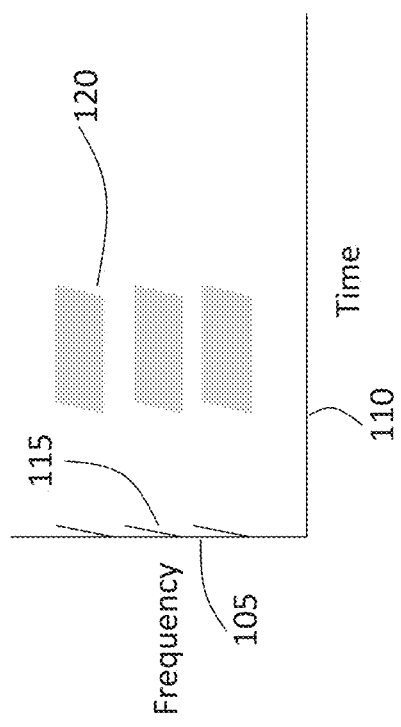
FIG. 5 shows plural simultaneously transmitted forward chirp signals and received echo signals.

FIG. 5 shows plural simultaneously transmitted forward chirp signals and echo signals 120 received from aperture 60. Each forward chirp signal 115 has a frequency range 105 and increases over a time segment 110. Echo signals 120 will be received from aperture 60 after chirp signals 115 are transmitted.

Figure 6:
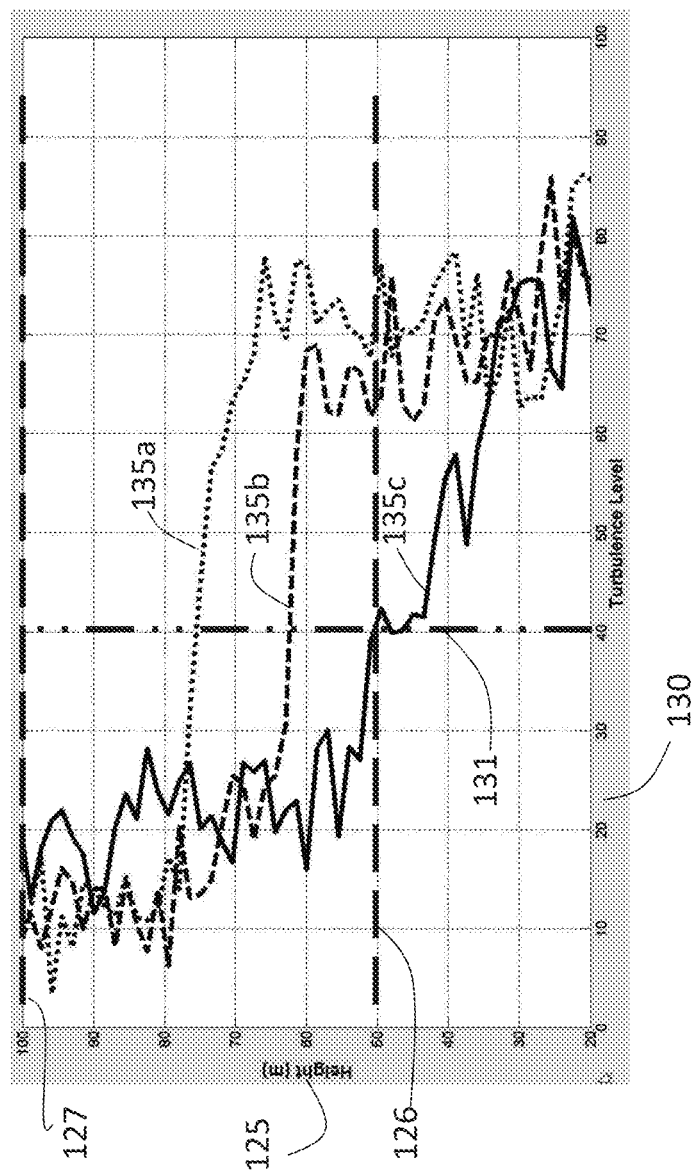
FIG. 6 shows signals backscattered from turbulence for one receiver channel at different times.

FIG. 6 shows backscattered signals 135a, 135b and 135c for one receiver channel after processing in a matched filter receiver implemented in computer 10, as described below with reference to FIG. 15. The signals 135a, b, c, are backscattered from turbulence that is within beam 26 of transmitter antenna 25. The height of turbulence from the ground is represented by height scale 125 with an aperture bottom 126 at height 50 m from the ground and an aperture top 127 at 100 m from the ground. The amplitude of the turbulence is represented by turbulence level scale 130 with a turbulence threshold 131 of 40. The measurements 135a, b, c, of turbulence are shown at 49, 56 and 63 seconds respectively after an aircraft has passed. The first two turbulence measurements 135a and 135b have turbulence above threshold value 131 that is above the bottom of the aperture 126 and is due to aircraft induced wake turbulence. The third turbulence measurement 135c has a turbulence that is below the bottom of aperture 126 and is due to background turbulence level of the atmosphere being other than aircraft induced wake turbulence. Although turbulence 135c is above turbulence threshold 131 the turbulence is below the bottom of aperture 126. In this case the turbulence in the aperture has demised below a safe threshold 131 after 63 seconds.

Figure 7:
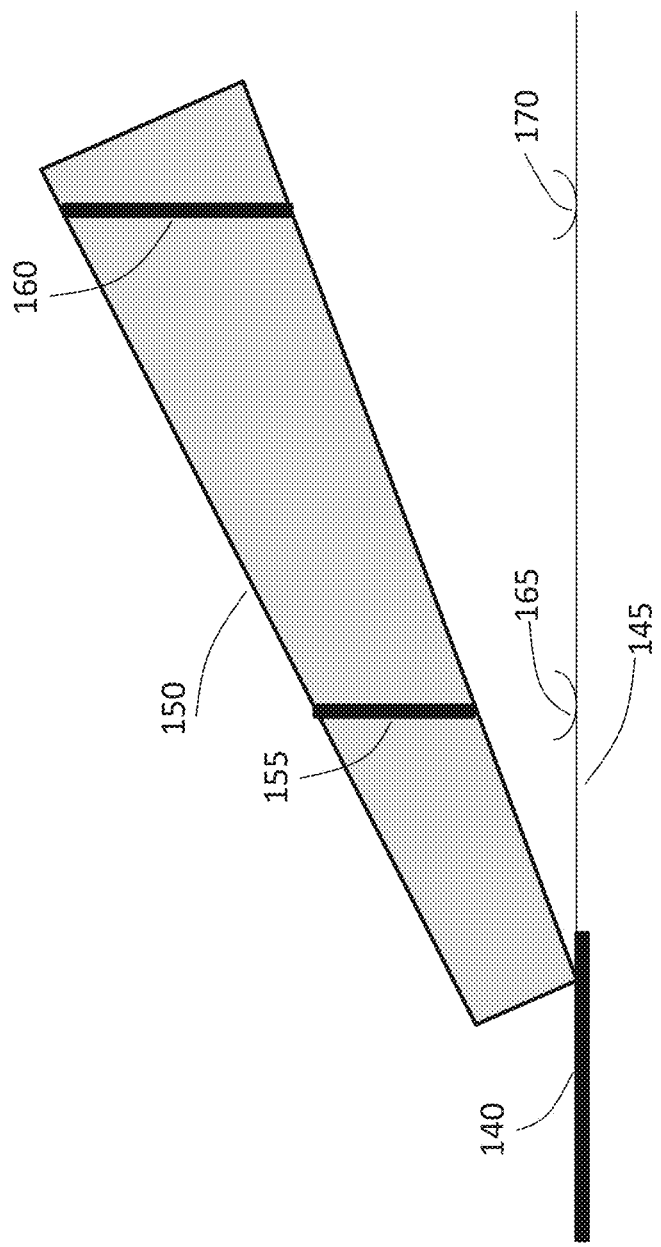
FIG. 7 shows an approach or departure corridor near an airport runway with apertures within the corridor.

FIG. 7 shows an airport runway 140, approach or departure corridor 150 and apertures 155 and 160 along the corridor 150 relative to ground level 145. Transmitter and receiver arrays 165 and 170 are located under apertures 155 and 160 respectively.

Figure 8:
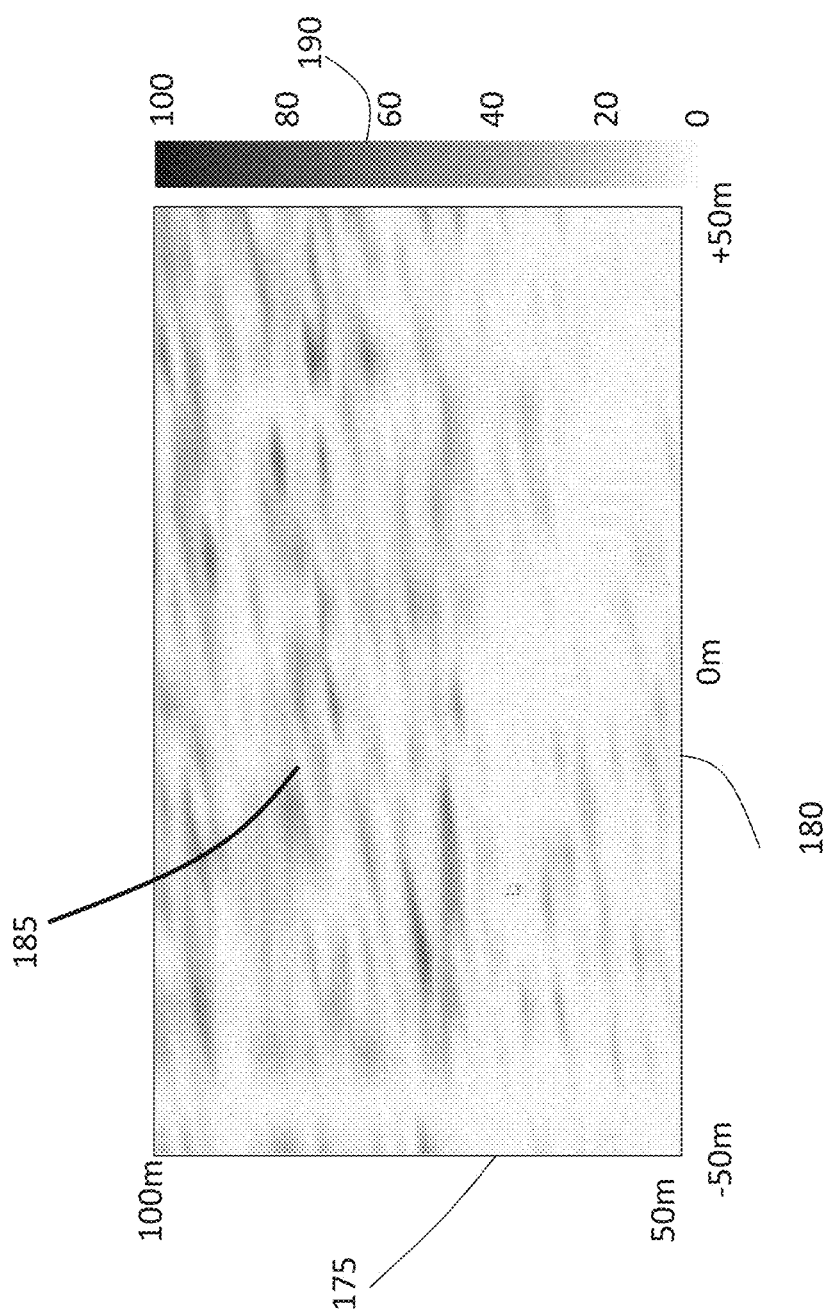
FIG. 8 shows a representation of turbulence measured with 20 transmitters and receivers when turbulence is relatively low and due to background atmospheric turbulence only being other than aircraft induced wake turbulence.

FIG. 8 shows relatively low turbulence in an aperture with no aircraft induced turbulence present but only background atmospheric turbulence being other than aircraft induced wake turbulence. The width 180 of the aperture is 100 m, plus and minus 50 m centred on a runway centreline. The height 175 of the aperture is from 50 to 100 m above ground. The turbulence greyscale 190 shows the level from 0 to 100 of turbulence 185 in the aperture. The lighter end of the greyscale represents the lower levels of turbulence.

Figure 9:
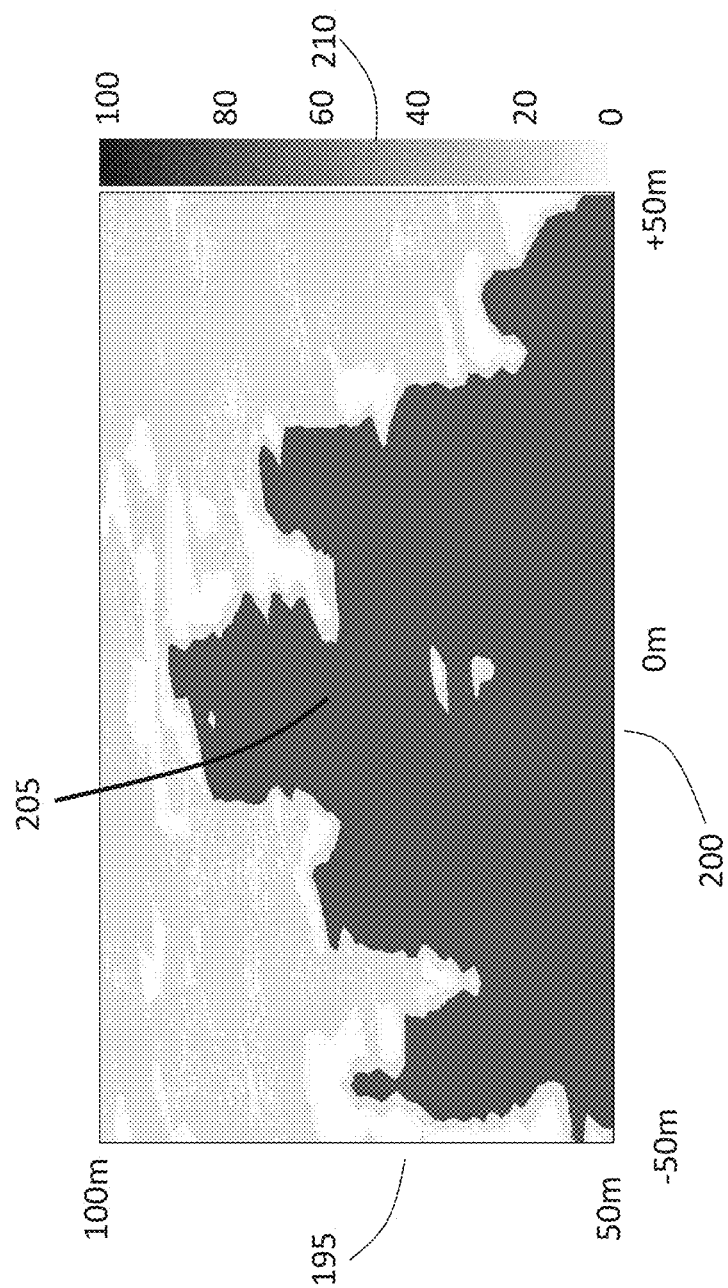
FIG. 9 shows a representation of turbulence measured with 20 transmitters and receivers when turbulence is relatively high and due to aircraft induced wake turbulence.

FIG. 9 shows relatively high turbulence in an aperture with aircraft induced turbulence present. The width 200 of the aperture is 100 m, plus and minus 50 m centred on a runway centreline. The height 195 of the aperture is from 50 to 100 m above ground. The turbulence greyscale 210 shows the level of turbulence 205 in the aperture. The darker end of the greyscale represents the higher levels of turbulence. For example an encounter with a turbulence level 80 on the greyscale may result in a severe roll of the aircraft greater than 45 degrees. In contrast an encounter with turbulence at a set threshold or level of 40 may be barely noticeable.

The time taken for the turbulence to reduce from that shown in FIG. 9 to that shown in FIG. 8 is the turbulence demise time. After the turbulence has reduced to the level shown in FIG. 8, it is safe for another aircraft to pass through the aperture on either an approach or departure corridor. The turbulence demise time may be broadcast to other aircraft by existing systems such as ACARS or sent directly to an air traffic control system by conventional communications means.

Figure 10:
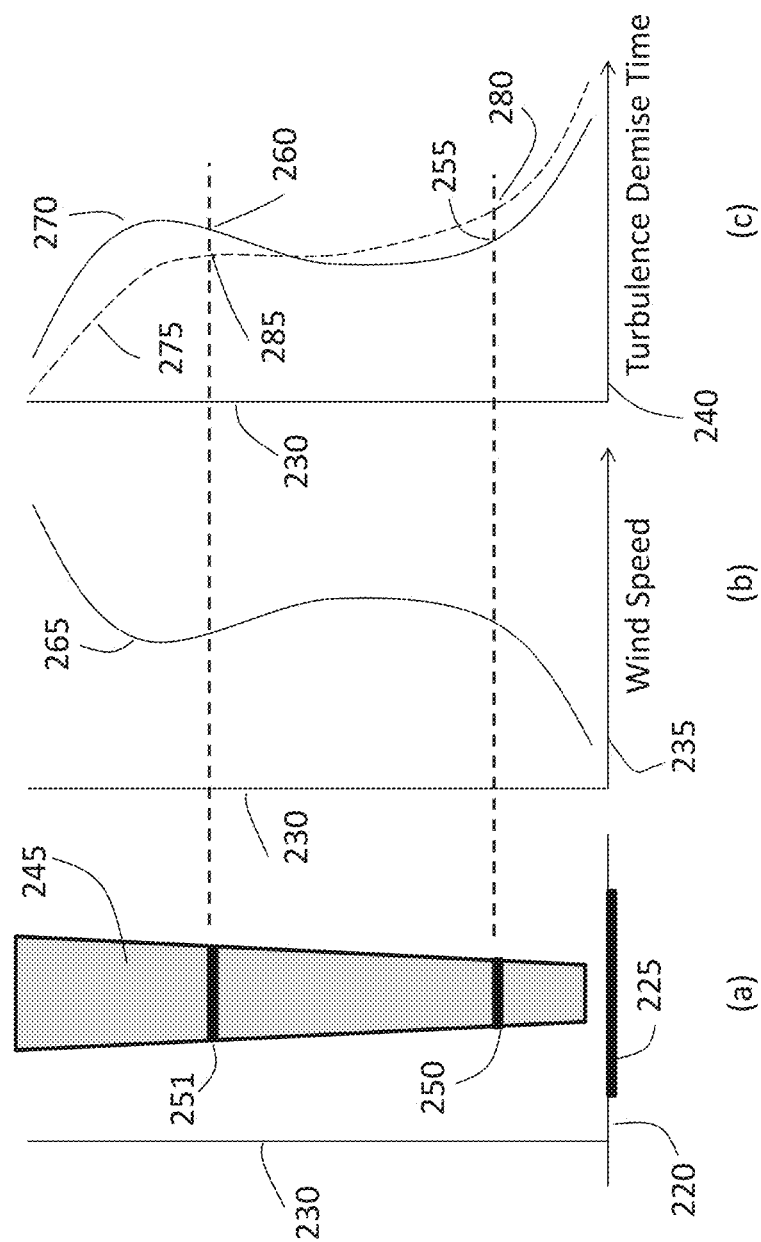
FIGS. 10a-10c show a runway corridor, a wind profile and a turbulence demise time along the corridor wherein the turbulence demise time is obtained in conjunction with the wind profile.

FIGS. 10a to 10c show a runway corridor, an associated wind profile and an associated turbulence demise time respectively along the corridor wherein the turbulence demise time is obtained in conjunction with the wind profile. FIG. 10a shows ground level 220, runway 225 viewed from the approach or departure end, approach or departure corridor 245, height 230 above ground, and two apertures 250, 251 at different heights within corridor 245. FIG. 10b shows a wind profile 265 including wind speed 235 across runway 225 against height 230. Demise time for wake turbulence may be considered to be the time that it takes cross wind 265 to blow wake turbulence 205 out of apertures 250, 251.

Referring to FIG. 10c an estimated profile 270 of wake turbulence demise time 240 may be obtained by dividing aperture width 41 (refer FIG. 2) by cross wind speed 265. Since turbulence demise time may be governed by factors other than cross wind, the estimated profile 270 of wake turbulence demise time shown in FIG. 10c needs to be corrected by obtaining measurements of actual turbulence demise time. This may be done by correcting the estimated demise time 270 at heights at which actual measurements of demise time are obtained from apertures 250, 251 by translating estimated demise times 255, 260 to actual demise times 280, 285. A complete profile of actual demise times 275 may then be obtained by interpolation using estimated demise time 270 and new values 280 and 285.

Figure 11:
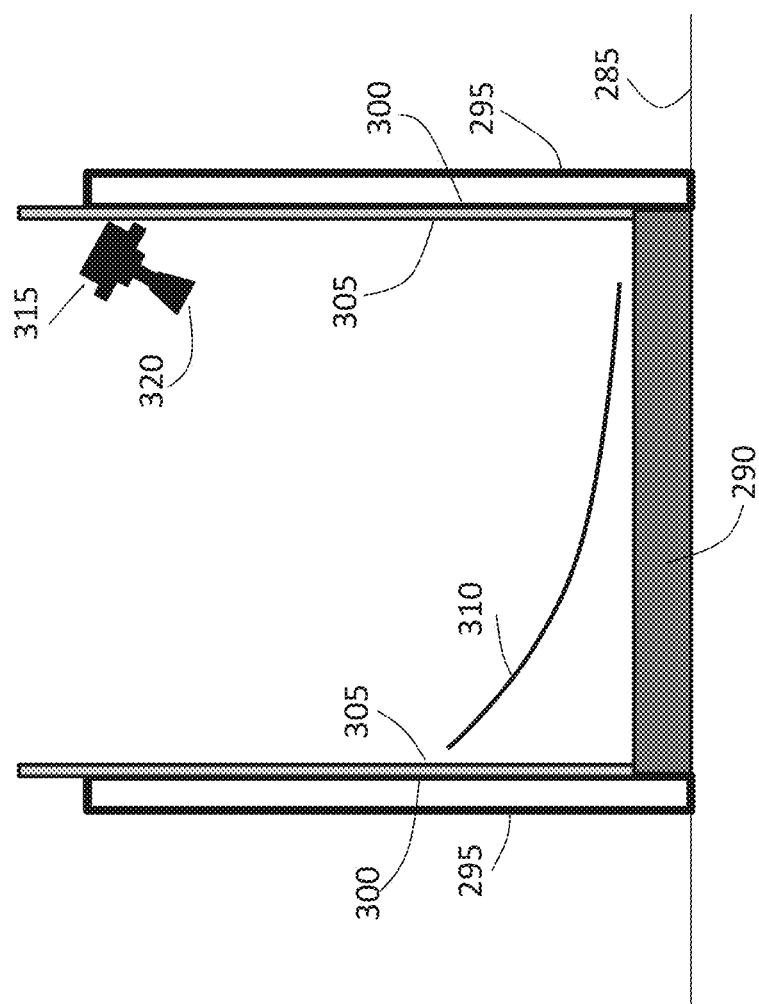
FIG. 11 shows an improved transmitter and receiver acoustic antenna structure for providing a relatively low side lobe beam with high efficiency and good isolation.

FIG. 11 shows a cross sectional view of a high performance antenna structure having characteristics of relatively high efficiency, low side lobe levels and excellent isolation, these characteristics being useful for accurate measurement of air turbulence. Such an antenna structure may be used for both transmitter and receiver. The antenna structure may be placed on ground 285 and pointed vertically. The antenna structure may be held to ground 285 by base 290. The side walls of the antenna structure may be round or square and made of layers 295 and 300 of HDPE 8 mm thick plastics separated by 50 mm of air. On the internal side a relatively high quality UV stabilised acoustic absorbent foam 305 may extend above the edge of the two outer layers to minimise diffraction of sound waves over the edge of the two outer sections. Offset parabolic reflector 310 may include a satellite antenna type Prodelin series 1123 of 1.2 m diameter. Driver 315 may include a BMS audio type 4591 with 40 degree horn 320 attached. Horn 320 may provide correct illumination of parabolic reflector 310 to ensure optimum efficiency and relatively low side lobe levels.

Figure 12:
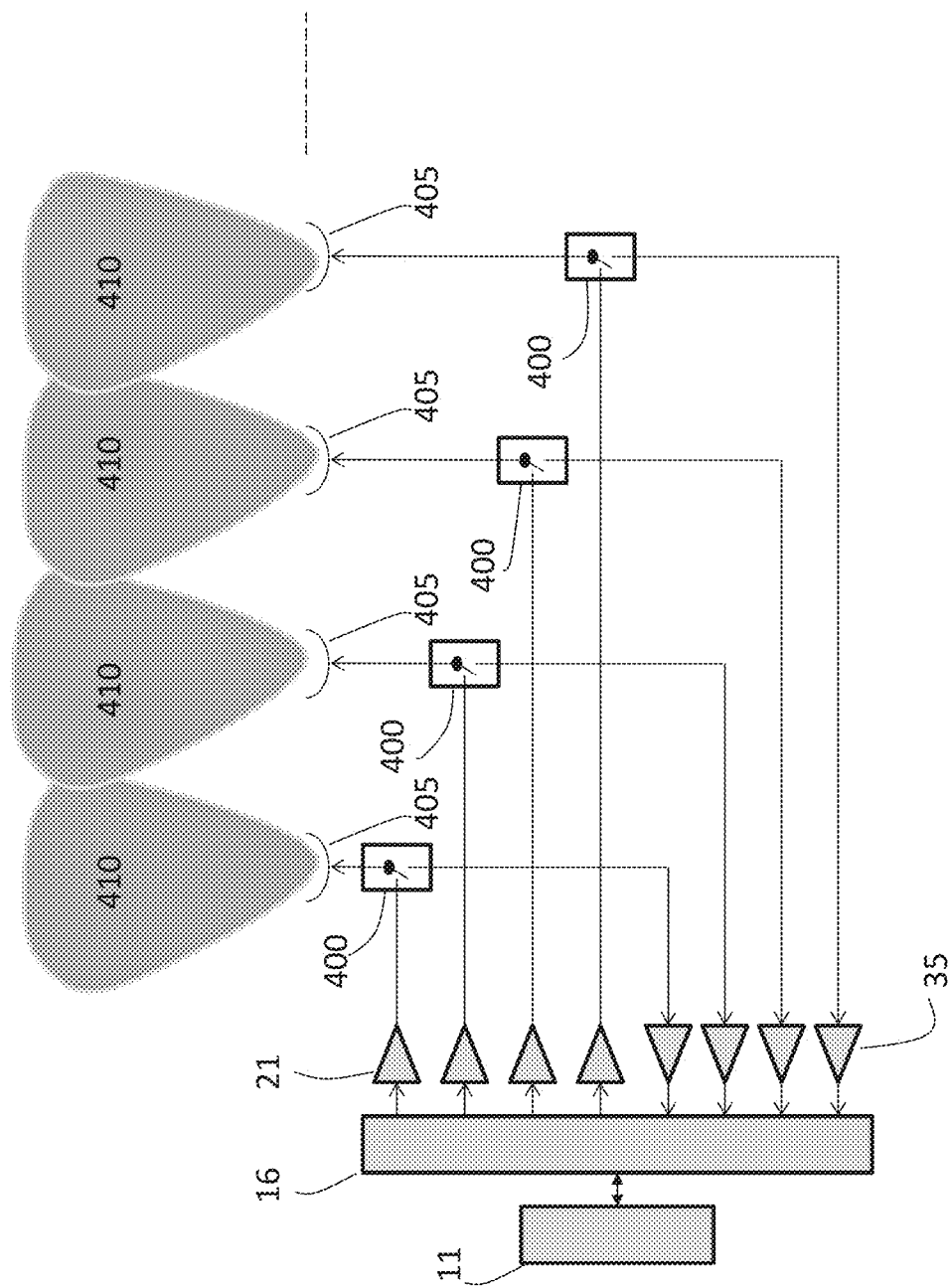
FIG. 12 shows a modified arrangement of transmitter and receiver antennas wherein the transmitter and receiver antennas comprise the same physical device.

FIG. 12 shows a modified arrangement of transmitter and receiver antennas wherein the transmitter and receiver antennas comprise the same antenna device 405 each having beam shape 410. A changeover switch 400 may be operated by computer 11 so that during the time that a chirp pulse signal is being transmitted, switch 400 connects antenna 405 to transmitter amplifier 21. At the end of the transmit pulse, switch 400 may be changed over so that antenna 405 is connected to receiver preamplifier 35. This arrangement may halve the number of antennas 405 but also sets a minimum range for a measurement while transmitter amplifier 21 is connected to antenna 405. The minimum range is the pulse length of the transmitted chirp multiplied by half the speed of sound.

Figure 13:
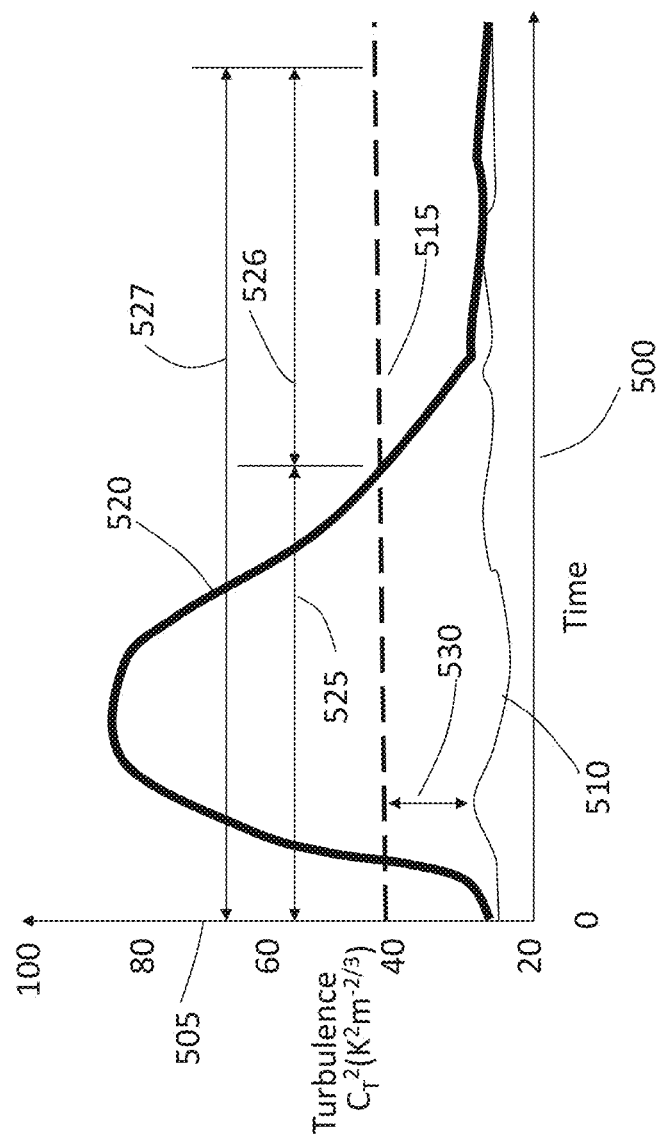
FIG. 13 shows a process for deriving aircraft spacing from turbulence demise time.

FIG. 13 shows an example of a process for measuring the time after an aircraft has passed through an aperture until the turbulence in the aperture falls below a set threshold. The time axis 500 starts from zero when an aircraft passes through the aperture and turbulence axis 505 shows the actual level of the turbulence 520 obtained from repeated measurements of turbulence. Level 515 is the set turbulence threshold of 40, below which it may be safe for another aircraft to pass through the aperture. Aircraft induced turbulence 520 will initially rise above background turbulence level 510 and will eventually return to that level after a period of time. Because atmospheric background turbulence varies significantly over time, a running average of the background turbulence level is needed to establish the current atmospheric turbulence 510 from which an appropriate level of 515 aircraft induced wake turbulence may be discriminated or obtained by adding a margin 530 to atmospheric turbulence 510. The period of time between the aircraft passing through the aperture at time 0 and the turbulence falling below the set threshold value is the turbulence demise time 525. By adding a safety margin 526 to the turbulence demise time 525 an aircraft spacing time 527 may be arrived at.

Figure 14:
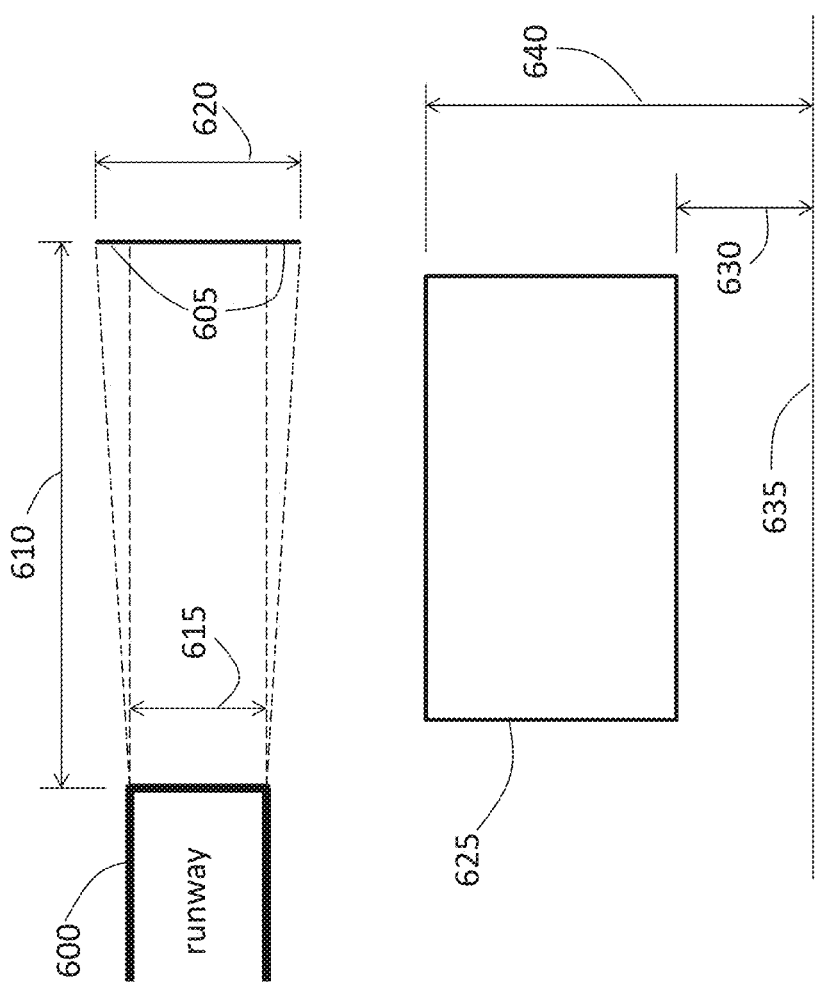
FIG. 14 shows an aperture being measured relative to a runway.

FIG. 14 shows how an aperture may be measured relative to runway 600. Runway 600 forms the basis calculating aperture width 620. The distance of the aperture from the runway 610 may be multiplied by 0.03 to obtain side margins 605. Side margins 605 may be added to runway width 615 to obtain the aperture width 620. The height 630 of the bottom side of aperture above ground 635 is known as an obstacle clearance surface and is specific to each runway approach. The height 640 of the aperture is the height of the aircraft approach path at the location of the aperture.

Figure 15:
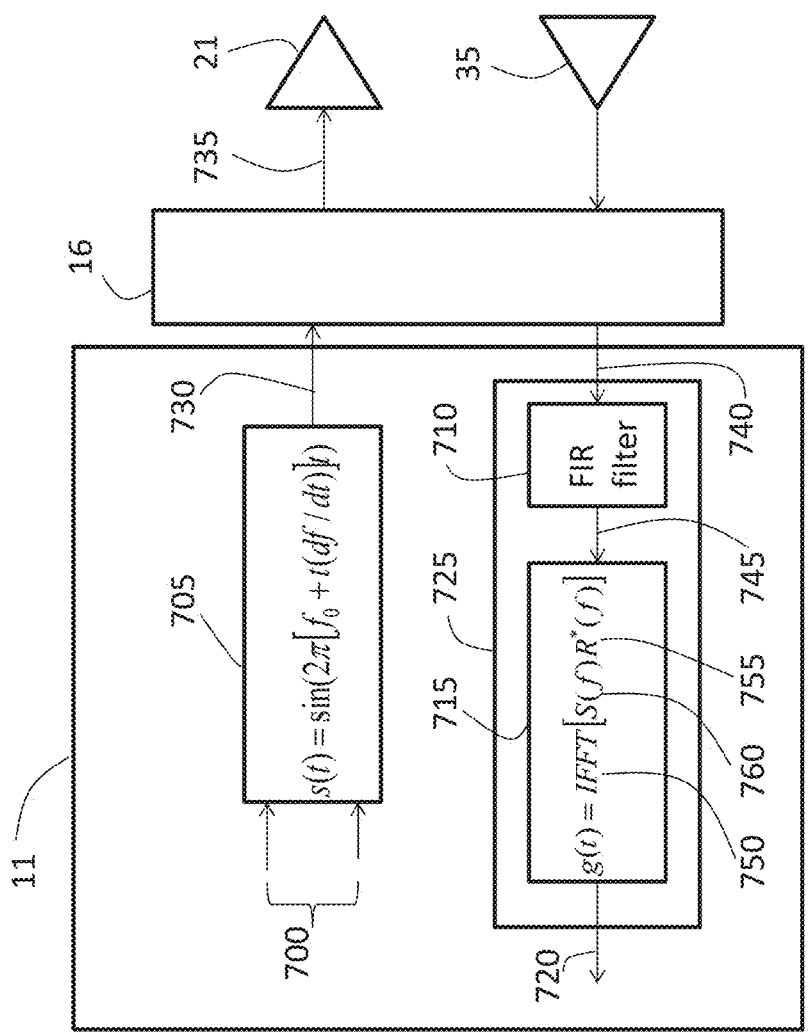
FIG. 15 shows elements of computer 11 in FIG. 12.

FIG. 15 shows elements of computer 11 in FIG. 2. Computer 11 contains chirp parameter inputs 700 such as fo and t(df/dt) (chirp rate). Digitally generated chirp 730 is applied to a D/A converter within sound card 16 to generate an analog chirp signal 735 to be applied to power amplifier 21. The received analog echo signal is applied to preamplifier 35 and then to a A/D converter within sound card 16 to generate a digital output 740. Digital output 740 is applied to a matched filter receiver 725. Matched filter receiver 725 has two components, namely input FIR digital filter 710 which selects a frequency range of interest to be applied to matched filter 715. Matched filter 715 operates in the frequency domain wherein a magnitude output 720 of the received signal is obtained from inverse FFT 750 after the received and filtered digital signal 745 is multiplied (755) in the frequency domain by an inverse 760 of the transmitted chirp. Magnitude output 720 may provide a direct indication of level of turbulence in the atmosphere and may be used to provide atmospheric turbulence data 510 and actual level of turbulence 520 (refer FIG. 13).

Finally, it is to be understood that various alterations, modifications and/or additions may be introduced into the constructions and arrangements of parts previously described without departing from the spirit or ambit of the invention

The invention claimed is:

1. A method for detecting atmospheric turbulence including aircraft induced wake turbulence and/or wind shear within an aperture associated with an aircraft approach or departure corridor around an airport, said method comprising: transmitting into said aperture acoustic signals having a waveform suitable for pulse compression; receiving backscattered acoustic echoes of the acoustic signals from said aircraft induced wake turbulence and/or wind shear, wherein said backscattered acoustic echoes are received via plural receiver antennas; processing the backscattered acoustic echoes in a matched filter receiver to provide a measure of said aircraft induced turbulence and/or wind shear, wherein said processing includes emulating the matched filter receiver to determine a magnitude of said backscattered acoustic echoes received via said plural receiver antennas, said magnitude being indicative of a level of said aircraft induced wake turbulence and/or wind-shear within said aperture; discriminating said aircraft induced wake turbulence and/or wind shear to determine a demise time, the demise time being a time taken for said aircraft induced wake turbulence and/or wind shear to fall below a set threshold at least in said aperture; and comparing amplitude from each receiver antenna to establish a horizontal location of said aircraft induced wake turbulence and/or wind shear.

2. The method according to claim 1, wherein said acoustic signals are transmitted via plural transmitter antennas.

3. The method according to claim 2, wherein said plural transmitter antennas are placed substantially across said aircraft approach or departure corridor.

4. The method according to claim 2, wherein said plural acoustic signals are transmitted substantially on the same frequency and include positive and negative chirps.

5. The method according to claim 2, wherein said plural acoustic signals are transmitted on different frequencies and include positive and negative chirps.

6. The method according to claim 1, wherein said plural receiver antennas are placed substantially across said aircraft approach or departure corridor.

7. The method according to claim 1, wherein said discriminating includes differentiating between aircraft induced wake turbulence and background atmospheric turbulence being other than aircraft induced wake turbulence.

8. The method according to claim 1, wherein said demise time is calculated substantially along an entire aircraft approach or departure corridor.

9. The method according to claim 1, wherein said threshold is set such that it is safe for a following aircraft to pass through said aperture.

10. The method according to claim 1, wherein a safety margin is added to said demise time to obtain an aircraft spacing time.

11. A system for detecting atmospheric turbulence including aircraft induced wake turbulence and/or wind shear within an aperture associated with an aircraft approach or departure corridor around an airport, said system comprising: at least one transmitter antenna configured to transmit into said aperture acoustic signals having a waveform suitable for pulse compression; plural receiver antennas configured to receive backscattered acoustic echoes of the acoustic signals from said aircraft induced wake turbulence and/or wind shear; a matched filter receiver configured to process the backscattered acoustic echoes to provide a measure of said aircraft induced wake turbulence and/or wind shear, wherein said matched filter receiver includes an algorithm configured to emulate the matched filter receiver to determine a magnitude of said backscattered acoustic echoes received via said plural receiver antennas, said magnitude being indicative of a level of said turbulence and/or winds shear within said aperture, and wherein said algorithm includes comparing amplitude from each receiver antenna to establish a horizontal location of said aircraft induced wake turbulence and/or wind shear; and means for discriminating said aircraft induced wake turbulence configured to determine a demise time, the demise time being the time taken for said aircraft induced wake turbulence and/or wind shear to fall below a set threshold at lease in said aperture.

12. The system according to claim 11, including plural transmitter antennas configured to transmit said acoustic signals.

13. The system according to claim 12, wherein said plural transmitter antennas are placed substantially across said aircraft approach or departure corridor.

14. The system according to claim 12, wherein said plural acoustic signals are transmitted substantially on the same frequency and include positive and negative chirps.

15. The system according to claim 12, wherein said plural acoustic signals are transmitted on different frequencies and include positive and negative chirps.

16. The system according to claim 11, wherein said plural receiver antennas are placed substantially across said aircraft approach or departure corridor.

17. The system according to claim 11, when said means for discriminating includes an algorithm for differentiating between aircraft induced wake turbulence and background atmospheric turbulence being other than aircraft induced wake turbulence.

18. The system according to claim 11, wherein said demise time is calculated substantially along an entire aircraft approach or departure corridor.

19. The system according to claim 11, wherein said threshold is set such that it is safe for a following aircraft to pass through said aperture.

20. The system according to claim 11, wherein a safety margin is added to said demise time to obtain an aircraft spacing time.

* * * * *